United States Patent
Guy et al.

(10) Patent No.: US 9,304,069 B2
(45) Date of Patent: Apr. 5, 2016

(54) APPARATUS FOR WORKING ON HISTOLOGICAL SAMPLES

(71) Applicant: Leica Biosystems Nussloch GmbH, Nussloch (DE)

(72) Inventors: Andrew Guy, Victoria (AU); Stella Knorr, Victoria (AU); Hermann Ulbrich, Bad Schonborn (DE)

(73) Assignee: Leica Biosystems Nussloch GmbH, Nussloch (DE)

(*) Notice: Subject to any disclaimer, the term of this patent is extended or adjusted under 35 U.S.C. 154(b) by 0 days.

(21) Appl. No.: 14/188,034

(22) Filed: Feb. 24, 2014

(65) Prior Publication Data

US 2014/0273078 A1   Sep. 18, 2014

(30) Foreign Application Priority Data

Mar. 15, 2013   (DE) .................. 10 2013 204 646

(51) Int. Cl.
*A61B 10/00*   (2006.01)
*G01N 1/31*   (2006.01)
*G01N 1/30*   (2006.01)
*G01N 1/34*   (2006.01)

(52) U.S. Cl.
CPC ............. *G01N 1/312* (2013.01); *G01N 1/30* (2013.01); *G01N 1/34* (2013.01)

(58) Field of Classification Search
CPC ......................................... G01N 1/30
See application file for complete search history.

(56) References Cited

U.S. PATENT DOCUMENTS

| 6,151,744 A | 11/2000 | Ohtani et al. |
| 6,495,106 B1 | 12/2002 | Kalra et al. |
| 2005/0186114 A1* | 8/2005 | Reinhardt et al. ............... 422/65 |
| 2007/0044823 A1 | 3/2007 | Yamamoto et al. |
| 2007/0141849 A1 | 6/2007 | Kanno et al. |
| 2009/0155907 A1 | 6/2009 | Winther et al. |

FOREIGN PATENT DOCUMENTS

| CN | 2570765 Y | 9/2003 |
| DE | 10 2007 022 014 A1 | 11/2008 |
| DE | 10 2007 044 708 A1 | 3/2009 |
| GB | 2490764 A | 11/2012 |
| WO | 2007062649 A1 | 6/2007 |
| WO | 2012117294 A2 | 9/2012 |

* cited by examiner

*Primary Examiner* — Jyoti Nagpaul
(74) *Attorney, Agent, or Firm* — Sughrue Mion, PLLC

(57) ABSTRACT

The invention relates to an apparatus for treatment of histological samples. The apparatus includes at least a working station, in which the sample gets into contact with a liquid reagent. Further, the apparatus includes a purification device, which blows off at least a part of the reagent adhering to the sample and/or the sample holding arrangement by means of a gas flow, or which sucks off at least a part of the reagent adhering to the sample and/or a sample holding arrangement.

22 Claims, 1 Drawing Sheet

APPARATUS FOR WORKING ON HISTOLOGICAL SAMPLES

Figure 1:
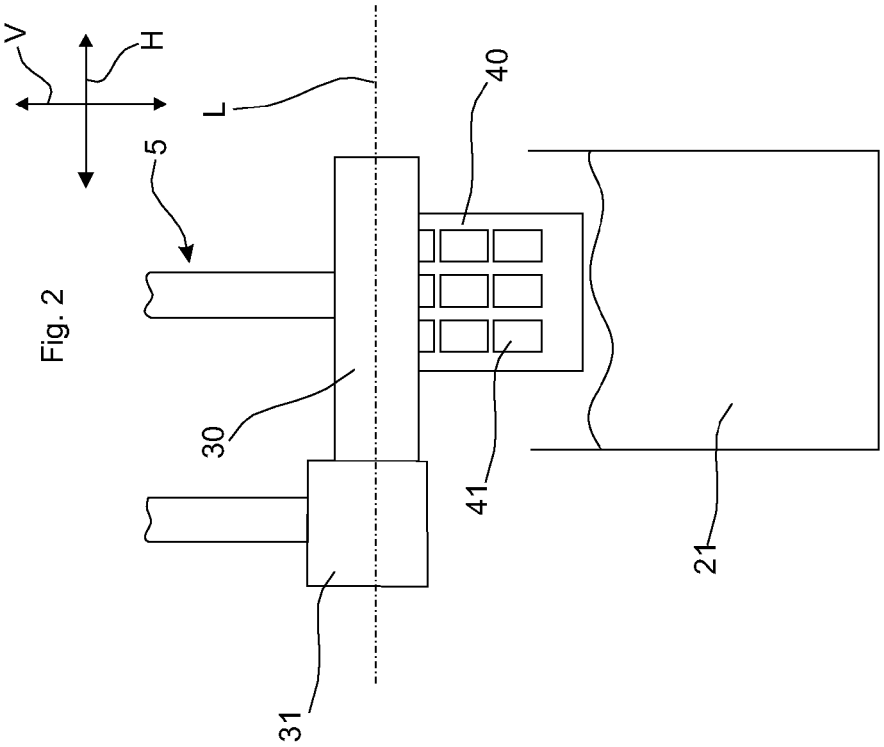

The invention relates to an apparatus for working on histological samples according to the preamble of claim 1.

The invention further relates to a method for working on histological samples.

It is the goal of the processing with, in most cases, a plurality of working stations to bring a sample taken from a patient into a condition, which allows for cutting into thin sections with a microtome. An ability to be cut may for instance be rendered possible in that in subsequent working steps a medium, which mechanically stabilizes the tissue, is introduced (infiltrated) into the tissue. Alternatively, the tissue may also be frozen.

From the prior art, a variety of working stations for working on histological samples is already known. As such, for instance, working stations of the types of cutting stations, fixing stations, dehydration stations, purifying stations, infiltration stations, embedding stations or microtomes (cutting stations) in executions of a wide variety are known.

In a cutting station the tissue, for instance taken from a patient, is cut to individual samples. In most cases, the samples are deposited in cassettes and are transported to a fixing station. A fixation of the samples is necessary, as the oxygen supply of the cells after removal of the tissue from the patient is inhibited, which leads to cell death. First, a swelling of cells can be observed and in addition, protein denaturation and autolysis occurs with subsequent bacterial digestion. In order to counteract these damages, a fixation of the extracted samples is executed in the fixing station with a fixing agent, such as formalin.

After treatment in the fixing station, a dehydration of the samples is executed in a dehydration station. A dehydration of the samples is necessary in order to enable the following process of infiltrating and embedding.

Since the fixing agent, particularly formalin, in most cases is an aqueous medium, while on the other hand the infiltrating or embedding agent to be used, in particular paraffin, in most cases is a medium non-miscible with water, a dehydration of the samples has to be carried out prior to further processing of the samples in a dehydration station. The dehydrating of the samples is carried out by means of a dehydration agent, such as for example ethanol.

Prior to a transfer of the samples to the infiltration station, they also are purified. A purification is necessary as the alcohol in the tissue of the sample is not miscible with paraffin. The alcohol therefore has to be removed from the tissue prior to the infiltration and be replaced by a reagent, which is miscible with paraffin, such as xylol.

After treatment of the sample in the purification station, it is transferred to an infiltration station. In the infiltration station, an infiltration agent, which in most cases corresponds to the embedding agent used later on, is introduced into voids of the sample to the point of saturation. Due to supplying of the infiltration agent, the samples may be mechanically stabilized.

After the processing of the sample in the infiltration station, it is processed in the embedding station. In the embedding station an embedding of the histological sample in an embedding agent is carried out, such as for instance paraffin or wax. In praxis, the term "embedding" is used in two ways. For one, as a synonym for "infiltrating", which is executed in the infiltration station as mentioned above, on the other hand it means the same as "embed" or "emblog", which is carried out in the embedding station.

For embedding, the samples are placed in forms, so called moulds, and the form is filled with the embedding agent. Subsequently, the histological sample is cooled such that the embedding agent may solidify. For cooling the histological samples, they for instance are set on a cooling plate of the embedding station. As a result, an embed-block is generated, in which the sample is fixed in place. After a hardening of the embedding agent, the sample may be cut with the microtome to individual thin sample sections, which may be dyed and observed with a microscope in a next step.

In order for the cutting process to be executed appropriately with the microtome, it is necessary, that the embed-block remains in a hardened condition. In praxis, a lab member then transports the cassettes in small groups, for instance on a tray, from the embedding station to the microtome.

In the apparatuses known from the prior art, the problem exists that during withdrawal of the histological samples or a sample holding arrangement from a reagent container such as for example a formalin container, a significant amount of the reagent liquid, such as for example formalin, remains adhered. During introduction of the samples and/or the sample holding arrangement into another reagent container, such as for example a dehydration agent container, this is also introduced along with it into the latter. The reagents of the subsequent reagent containers that way are quickly contaminated and/or used up and thus have to be replaced frequently, increasing the working expenses.

It is the objective of the invention to provide an apparatus for working on histological samples, in which at least a reagent contained in a reagent container is not or only slightly contaminated during the operation of the apparatus.

According to the invention, the apparatus for working on histological samples comprises at least one working station, in which at least one sample and/or one sample holding arrangement comes into contact with a liquid reagent. Further, the apparatus comprises a purifying device, which by means of a gas flow blows off at least a part of the reagent adhering to the sample and/or the sample holding arrangement. Alternatively, the purifying device sucks away at least a part of the reagent adhering to the sample and/or the sample holding arrangement.

The working station may be a fixing station and/or a dehydration station and/or a purifying station and/or an infiltration station and/or an embedding station and/or a dyeing station. In the sense of the invention, the working station may be any station, in which the sample and/or the sample holding arrangement are wetted with a reagent. The reagent accordingly may be a fixing agent, a dehydration agent, a purifying agent, an infiltration agent, and embedding agent and/or a dyeing agent. The sample holding arrangement may be a cassette, which receives at least one sample. Alternatively or in addition, the sample holding arrangement may be a holding frame, receiving a variety of cassettes. Of course, the sample holding arrangement is not limited to the above mentioned implementations and thus may be any member, which is suitable for supporting the sample.

The advantage of the purifying device in the apparatus is that after a treatment of the sample by a reagent, a purification of the sample and/or the sample holding arrangement from the reagent may be effected by the purification device. As a result of the purification it is ensured that the adhering reagent is not introduced into the subsequent reagent container, such that a contamination of the subsequent reagent container is prevented. That way, the replacement interval of the reagents may be prolonged, thereby reducing the working expenses.

As already mentioned, the working station may be a purifying station, such as a water station. Here, as well, there is fundamentally the problem that the excessive water still adhering to the samples and/or to the sample holding arrangement would dilute the liquid in the subsequent reagent container. In an advantageous manner the present invention prevents that the excessive water has to be removed in a laborious and cumbersome way by additional rinsing, for instance with ethanol.

As discussed above, for dehydration of the sample, a dehydration agent is used, which essentially is ethanol. When using ethanol, however, the problem persists that particularly for an air supply, for instance due to the airflow for blowing off the adhering reagent off the sample and/or the sample holding arrangement, an ignitable mixture, for instance an air-ethanol-mixture, may form. By sucking off the reagent from the sample by means of the purifying device, formation of an ignitable mixture is prevented.

In a special implementation, a gas of the gas flow for blowing off the reagent off the sample and/or the sample holding arrangement may be an inert gas. By using an inert gas, it is also prevented, that an ignitable mixture, for instance an air-ethanol-mixture, forms.

The purifying device may be placable and/or may be positioned such that after processing the purifying device removes the reagent, which adheresto the sample and/or the sample holding arrangement. This happens before the sample and/or the sample holding arrangement is further conveyed and/or comes into contact with a further reagent. That way, in an easy way, it is secured that a purification of the sample and/or the sample holding arrangement takes place prior to an introduction into a regent container.

In particular, the purification device may be positioned in a region adjacent, in particular immediately adjacent, to the reagent container, situated above the reagent container. Thus, the purification happens immediately after withdrawal of the sample and/or the sample holding arrangement from the reagent container.

The gas stream exiting the purification device may at least partially be directed toward the reagent container, which at least partially collects the blown-off reagent. In particular, the gas flow may be directed such that an angle between the gas flow and an extension in length direction of the sample holding arrangement is smaller than 90°, in particular bigger than 0° and smaller than 90°, preferably 45°. Such an orientation of the gas flow yields the advantage that the reagent blown off the sample or the sample holding arrangement at least partially is resupplied into the reagent container such that a contamination of the apparatus with the reagent is prevented.

Alternatively, the sucked-off reagent flow may be directed toward a collection receptacle, which at least partially collects the sucked-off reagent. The collection receptacle thus serves for receiving the reagent sucked off the sample and/or the sample holding arrangement and may be arranged within or exterior to the purification device. Further, the collection receptacle may be releasably connected or formed in one piece with the purification device.

In a special embodiment, the purification device on the one hand and the sample and/or the sample holding arrangement on the other side, may be arranged movably with respect to one another. By the relative movement of the above mentioned components, an effective and quick purification of the sample and/or the sample holding arrangement may be achieved. Therein, the purification device may be formed stationary such that only the sample and/or the sample holding arrangement is moving relative to the purification device. Alternatively, the purification device may be formed movably such that a relative movement of the purification device with respect to the sample and/or the sample holding arrangement is possible.

A direction of movement of the purification device may be opposite to the direction of movement of the sample and/or the sample holding arrangement. Particularly, the sucking-off or blowing-off of the reagent adhering to the sample and/or the sample holding arrangement may be carried out during the movement of the sample and/or the sample holding arrangement. Thereby, the purification of the sample and/or the sample holding arrangement may be further enhanced.

In a preferred embodiment, the purification device may comprise at least one nozzle for blowing-off or sucking-off the reagent. By providing a nozzle, a gas flow with a high velocity may be achieved, being advantageous for the blowing-off of the reagent adhering to the sample and/or the sample holding arrangement.

For an especially advantageous embodiment of the apparatus according to the invention, the parameters for a blowing-off process and/or the parameters for a sucking-off process may be set individually. In particular, it may be provided in an advantageous way that the amount of gas of the gas flow streaming per time unit is adjustable and/or that the flow velocity is adjustable and/or that the profile of the gas flow is adjustable.

In particular, it may also be provided that various gas flows are adjusted in various areas of the purification device and/or are preselected. The advantage of an adjustment of the mentioned parameters is that the purification process may be adapted to the particular conditions. For a purification of a support frame, in which the samples only adhere to small holding plates (slides), the velocity of the gas flow has to be chosen smaller than for a support frame, in which the samples are arranged in cassettes. The parameters for instance may be preselectable and/or adjustable depending on the working station and/or the viscosity of the reagents.

Alternatively or in addition it may also be provided that the temperature of the gas is adjustable and/or that the period of a blowing-off process is adjustable and/or that the period of a sucking-off process is adjustable and/or that a switching time between a sucking-off process and a blowing-off process is adjustable and/or that the sucking volume per time unit is adjustable.

The nozzle may comprise an opening, in particular an elongated opening, the direction of its lengthwise extension at least substantially being arranged perpendicular to the moving direction of the purification device and/or the sample and/or the sample holding arrangement. In particular, the nozzle may be wider in a direction of lengthwise extension than the sample and/or the sample holding arrangement. Due to such design of the nozzle, it may in an easy way be achieved that the reagent is sucked-off or blown-off along the entire direction of lengthwise extension of the sample and/or the sample holding arrangement.

The purification device may comprise two nozzles, wherein the sample and/or the sample holding arrangement is arranged between the two nozzles. The nozzles may be oriented in parallel to one another. By arranging the sample and/or the sample holding arrangement between two nozzles, it may be achieved that the reagent is sucked-off from two sides off the sample and/or the sample holding arrangement or that the gas flow is blown onto the sample arrangement from sideways. Thereby a fast purification of the sample and/or the sample holding arrangement is possible. The nozzles may have mirror image symmetry with respect to the sample and/or the sample holding arrangement.

The purification device, in particular the nozzle, may comprise at least two openings. The openings may be arranged next to and/or on top of another. The orientation of the openings with respect to each other may be formed differently such that in a sucking-off process or a blowing-off process different gas flow directions are created. Due to such a design of the openings, swirls may be realized in the gas flow increasing the purification effect.

Further, two adjacent nozzles may be swiveled each around its length axis with respect to one another. As a consequence of the deviation of the nozzles, the openings of the nozzles at least partially point to the sample and/or the sample holding arrangement. Consequently it is ensured that the gas flow exiting from the nozzles impinges the sample and/or the sample holding arrangement and the adhering reagent is resupplied into the reagent container. Thereby, a contamination of the apparatus is prevented. Alternatively, it is ensured that the reagent situated on the sample and/or the sample holding arrangement is sucked-off by means of the nozzles.

In particular, the apparatus according to the invention may be formed both for blowing off at least a part of the reagent adhering to the sample and/or to the sample holding arrangement by means of a gas flow as well as for sucking-off at least a part of the reagent adhering to the sample and/or the sample holding arrangement and having a switching device provided for switching between a blowing-off and a sucking-off.

In a special embodiment, the apparatus comprises a switching device by means of which it may be selected whether a blowing-off process or a sucking-off process is effected by the purification device. Thus, the purification process to be carried out by the purification device, preferably for each working station, may be adjusted individually. Thus, during purification, the different physical properties of the reagents, such as for instance the viscosity, may be taken into account.

The reagent may be supplied during the blowing-off process either to the reagent container or to a collection container adjacent to the reagent container. During a sucking-off process, the sucked-off reagent may be collected in the collection receptacle for disposal.

In a special embodiment, a control device is provided in which for at least one working station, in particular for each working station, the parameters for controlling the purification device are deposited and are accessed and applied when needed, preferably automatically.

For example, it may be defined for at least one parameter whether a sucking-off or a blowing-off should be executed or whether multiple sucking-off and blowing-off processes should be executed alternatingly. Alternatively or in addition at least one parameter may concern the amount of gas of the gas flow per time unit, or the flow velocity, or the profile of the gas flow, or the gas temperature, or a sucking-off velocity or a sucking volume per time unit, or the period of a sucking-off process or the period of a blowing-off process.

In a particular embodiment of the apparatus according to the invention, a cooling device for cooling the gas is provided. This embodiment has the very particular advantage that the samples to be purified may be cooled at the same time during the purification process. This, for example, is of advantage, if the samples were treated with paraffin and a fast solidifying of the paraffin is desired.

Alternatively or in addition, the apparatus according to the invention may comprise a heating device for heating the gas. Such a device allows heating of the sample at the same time during a purification process; this, for instance, to fluidfy paraffin.

A further objective of the invention is to provide a method for working of histological samples, preventing or reducing contamination of the respective reagent contained in the reagent containers. This objective is achieved with a method for treating histological samples, using the apparatus as described above.

As already mentioned in general, in a particular embodiment it may be adjusted specifically for one, in particular more, working station whether a purification process is executed by sucking-off or blowing-off of the reagent from the sample and/or the sample holding arrangement. Further, it may be adjusted for at least one, in particular more, working station that one of the blowing-off process and the sucking-off process and subsequently the other one of the blowing-off process and the sucking-off process is carried out. This yields the advantage, that the reagent is purified repeatedly, i.e. by the sucking-off and the blowing-off.

It may be provided that in a purification process first a blowing process is carried out and thereby the reagent to be removed is transported to a predetermined or a predeterminable collection site, for example a receptacle at the sample holding arrangement, from which it is subsequently sucked off. It is also possible, for example with a blowing flow directed in a special way, to blow off the reagent situated at the collection site.

In the drawing, the matter of the invention is illustrated schematically and will be described in the following with reference to the drawings, wherein same or equally acting elements in most cases are denoted with the same reference signs.

Figure 2:
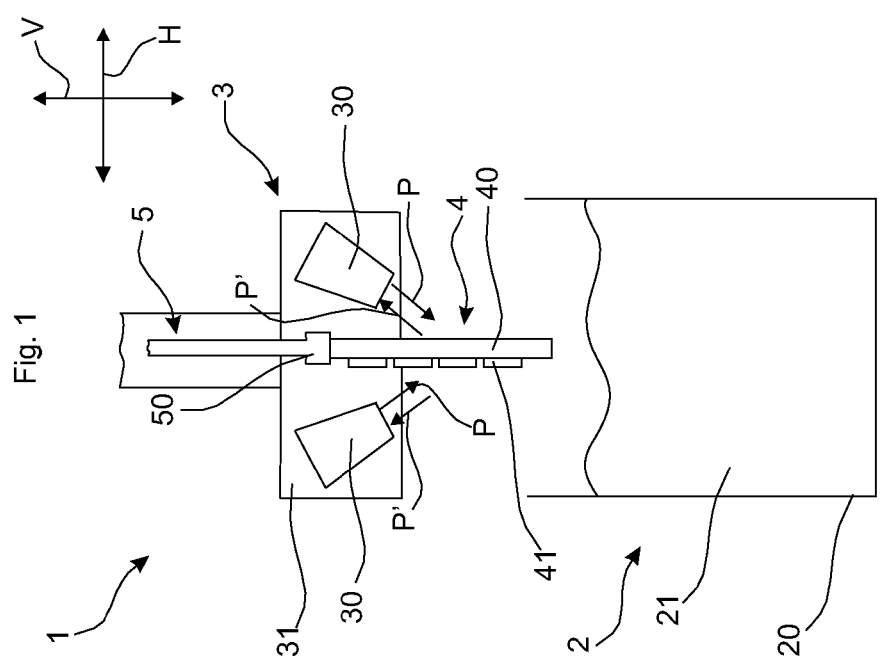

Therein show:

FIG. 1 a side view of the purification device according to the invention,

FIG. 2 a front view of the purification device according to the invention.

The apparatus 1 shown in FIGS. 1 and 2 comprises a working station 2, such as a fixing station. The working station 2 serves for treating histological samples not shown which are attached to a sample holding arrangement 4. For this, the working station 2 comprises a reagent container 20, in which a liquid reagent 21, such as formalin, is contained. The liquid reagent 21 for treatment of the histological sample is brought in contact with the latter. Of course, the working station 2 may alternatively be a dehydration station and/or an infiltration station and/or an embedding station and/or a dyeing station and/or a purification station.

The sample holding arrangement 4 comprises a support frame 40, which supports a variety of cassettes 41, wherein in the cassettes 41 at least one histological sample to be treated is arranged. The cassettes 41 are arranged at or at least partially in the support frame 40 in a matrix form. During the treatment of the histological samples, the sample holding arrangement 4 is situated in the container 20 such that the cassettes 41 and thus the samples are entirely wetted by the reagent 21.

The apparatus 1 comprises a transport device 5 for withdrawing the sample holding arrangement 4 from the reagent container 2. The transport device 5 at least in a vertical direction V is movable and comprises a gripper 50, which may be releasably connected to a part of the support frame 40. The connection may be form fitted, for instance due to a latching connection. Due to the connection between the gripper 50 and the support frame 40 it is ensured that the support frame 40 may move together with the transport device 5 in a vertical direction.

The transport device 5 transports the sample holding arrangement 4 from the working station 2 shown in FIG. 1 to a next working station not shown. For this purpose, the transport device 5 may execute a movement in horizontal direction H besides a movement in vertical direction V.

The apparatus 1 further comprises a purification device 3, which is arranged above the working station 2. The purification device 3 comprises two nozzles 30, which are swiveled to one another with respect to a length axis L shown in FIG. 2. The nozzles 30 are oriented in parallel to one another and are arranged as mirror images to one another with respect to the sample holding arrangement 4. Further, the nozzles 30 are spaced from one another such that the sample holding arrangement 4 and the transport device 5 may be moved within an area situated between the nozzles 30, in particular in a vertical direction, without abutting against the nozzles 30.

The nozzles 30 each comprise an opening at their front side directed toward the sample holding arrangement 4, through which the gas flow for blowing the reagent off the sample and/or the sample holding arrangement is blown-off. Alternatively, the air-reagent mixture sucked-off of the sample and/or the sample holding arrangement enters into the nozzle through the opening.

As is apparent from FIG. 2, the nozzle is wider in a direction of lengthwise extension than the support frame 40. The nozzles 30 extend transversal, in particular perpendicular, from a nozzle support 31 with respect to the vertical moving direction V of the sample holding arrangement 4. The nozzle support 31 is formed movably in vertical direction V and in horizontal direction H.

During retraction of the samples and/or the sample holding arrangement 4 from the working station 2, it is moved past the nozzles 30. In a first mode of operation, a gas flow, in particular an air flow, flows from the nozzles 30 in a direction P toward the samples and/or the sample holding arrangement. The gas flow causes a blowing-off of the reagent adhering to the samples and/or the sample holding arrangement 4. Since the nozzles 30 are arranged swiveled with respect to one another along the length axis L, the air flow exiting the nozzle 30 impinges on the samples and/or the sample holding arrangement in a transversal way. In particular, the gas flow impinges on the sample and/or the sample holding arrangement 4 in an angle bigger than 0° and smaller than 90° with respect to a length extension of the sample holding arrangement 4 in vertical direction V.

In a second mode of operation, a low pressure is applied within the nozzles 30 such that an air-reagent mixture flow flows from the samples and/or the sample holding arrangement 4 in a direction P' into the nozzles 30. From there, it flows to a collection receptacle not shown.

LIST OF REFERENCE SIGNS

1 apparatus
2 working station
3 purification device
4 sample holding arrangement
5 transport device
20 reagent container
21 liquid reagent
30 nozzle
31 nozzle support
40 support frame
41 cassette
50 gripper
H horizontal direction
L length axis of the nozzle
V vertical direction

The invention claimed is:

1. An apparatus for treatment of histological samples with at least a working station, in particular a fixing station and/or a dehydration station and/or a purification station and/or an infiltration station and/or an embedding station and/or a dyeing station, in which the sample and/or a sample holding arrangement comes into contact with a liquid reagent, the apparatus comprising:
   a purification device configured to:
      blow off, by means of a gas flow, at least a part of a reagent adhering to the sample and/or the sample holding arrangement, or
      suck off at least a part of a reagent adhering to the sample and/or the sample holding arrangement,
   wherein the purification device comprises a plurality of nozzles configured to blow off or suck off the reagent, and
   wherein the sample and/or the sample holding arrangement is arranged between two nozzles of the plurality of nozzles.

2. The apparatus according to claim 1, wherein a gas of the gas flow is an inert gas.

3. The apparatus according to claim 1, wherein the purification device may be positioned and/or is positioned such that the purification device removes the reagent adhering to the sample and/or the sample holding arrangement after a processing, prior to transporting the sample and/or the sample holding arrangement further and/or getting into contact with another reagent.

4. The apparatus according to claim 1, wherein the gas flow is directed at least partially onto a reagent container, the reagent container being configured to collect at least a portion of the blown-off reagent.

5. The apparatus according to claim 1, wherein the sucked-off reagent flow is directed toward a collection receptacle which at least partially collects the sucked-off reagent.

6. The apparatus according to claim 1, wherein the purification device on the one hand and the sample and/or the sample holding arrangement on the other hand are arranged movably with respect to another.

7. The apparatus according to claim 1, wherein at least one of
   a. a moving direction of the purification device is opposite to a moving direction of the sample and/or the sample holding arrangement, and
   b. a moving direction of the purification device is opposite to a moving direction of the sample and/or the sample holding arrangement, wherein during the movement the sucking-off or blowing-off is carried out.

8. The apparatus according to claim 1, wherein a nozzle of plurality of nozzles comprises an elongated opening, the direction of its lengthwise extension being arranged perpendicular to the moving direction of the purification device and/or the sample and/or the sample holding arrangement.

9. The apparatus according to claim 1, wherein two adjacent nozzles of the plurality of nozzles each are swiveled around their length axis (L) with respect to each other.

10. The apparatus according to claim 1, wherein the plurality of nozzles are arranged as mirror images to one another with respect to the sample and/or the sample holding arrangement.

11. The apparatus according to claim 1, wherein a nozzle of the plurality of nozzles is wider in a direction of the lengthwise extension than the sample and/or the sample holding arrangement.

12. The apparatus according to claim 1, wherein at least from among:
   a. the amount of gas of the gas flow per time unit is adjustable,
   b. the flow velocity is adjustable,
   c. the profile of the gas flow is adjustable,
   d. the temperature of the gas is adjustable,
   e. the period of a blowing-off process is adjustable,
   f. the period of a sucking-off process is adjustable,
   g. the switching time between a sucking-off process and a blowing-off process is adjustable, and
   h. the sucking volume per time unit is adjustable.

13. The apparatus according to claim 1, wherein a nozzle of the plurality of nozzles comprises at least two openings for sucking-off and/or blowing-off, the two openings being aligned in different ways with respect to one another.

14. The apparatus according to claim 1, wherein
   the apparatus is configured to both blow off at least a part of the reagent adhering to the sample and/or the sample holding arrangement by means of a gas flow, and to suck off at least a part of the reagent adhering to the sample and/or the sample holding arrangement, and
   the apparatus further comprises a switching device configured to switch between a blowing-off and a sucking off.

15. The apparatus according to claim 14, further comprising a control device is provided in which for at least a working station, in particular for each working station, the parameters for controlling the purification device are deposited and are accessed and applied if needed, preferably automatically.

16. The apparatus according to claim 15, wherein at least one parameter of the parameters for controlling the purification device defines whether a sucking-off or a blowing-off should be carried out or whether multiple sucking-off and blowing-off processes should be executed alternatingly.

17. The apparatus according to claim 15, wherein at least one parameter of the parameters for controlling the purification device concerns at least one from among a gas amount of the gas flow flowing per time unit, a flow velocity or profile of the gas flow, a gas temperature, a sucking-off velocity, a sucking volume per time unit, a period of a sucking-off process, and a period of a blowing-off process.

18. A method for treatment of histological samples by using an apparatus according to claim 1.

19. The method according to claim 18, wherein a blowing process is executed and thereby the reagent to be removed is transported toward a predetermined or predeterminable collection site, from which it subsequently is sucked off.

20. The apparatus according to claim 1, wherein the two nozzles of the plurality of nozzles are arranged in parallel with respect to each other.

21. An apparatus for treatment of histological samples comprising:
   a working station comprising a reagent container;
   a sample holding arrangement configured to hold samples and to immerse the samples and a portion of the sample holding arrangement in a liquid reagent container in the reagent container; and
   a purification device configured to at least one of
      blow off, by means of a gas flow, at least a part of a reagent adhering to the sample and/or the sample holding arrangement, and
      suck off at least a part of a reagent adhering to the sample and/or the sample holding arrangement,
   wherein the purification device comprises a plurality of nozzles configured to blow off or suck off the reagent, and
   wherein the sample holding arrangement is arranged between two nozzles of the plurality of nozzles.

22. The apparatus according to claim 20, wherein the purification device on the sample holding arrangement is movable with respect to the purification device.

* * * * *